(12) United States Patent
Gakh et al.

(10) Patent No.: US 8,420,815 B1
(45) Date of Patent: Apr. 16, 2013

(54) ANTI-CANCER AGENTS BASED ON N-ACYL-2, 3-DIHYDRO-1H-PYRROLO[2,3-B] QUINOLINE DERIVATIVES AND A METHOD OF MAKING

(75) Inventors: Andrei A. Gakh, Bethesda, MD (US); Mikhail Krasavin, Moscow (RU); Ruben Karapetian, Moscow (RU); Konstantin A. Rufanov, Moscow (RU); Igor Konstantinov, Moscow (RU); Elena Godovykh, Rostov-Na-Donu (RU); Olga Soldatkina, Moscow (RU); Andrey V. Sosnov, Moscow (RU)

(73) Assignee: U.S. Department of Energy, Washington, DC (US)

( * ) Notice: Subject to any disclaimer, the term of this patent is extended or adjusted under 35 U.S.C. 154(b) by 351 days.

(21) Appl. No.: 12/822,237

(22) Filed: Jun. 24, 2010

(51) Int. Cl.
*C07D 471/04* (2006.01)

(52) U.S. Cl.
USPC .............................................. 546/80; 546/81

(58) Field of Classification Search ................... 546/80, 546/81
See application file for complete search history.

(56) References Cited

FOREIGN PATENT DOCUMENTS

JP 03083986 * 4/1991

OTHER PUBLICATIONS

Synthesis and cytotoxic activity of substituted Luotonin A derivatives. Sabrina Dallavalle et al. 2004.*
Guan-Sai Liu et al, Expeditious Total Synthesis of Camptothecin and 10-Hydrocycamptothecon, 2008.*

* cited by examiner

*Primary Examiner* — Rita Desai
(74) *Attorney, Agent, or Firm* — Brian J. Lally; Michael J. Dobbs; John T. Lucas

(57) ABSTRACT

The present disclosure relates to novel compounds that can be used as anti-cancer agents in the prostate cancer therapy. In particular, the invention relates to N-acyl derivatives of 2,3-dihydro-1H-pyrrolo[2,3-b]quinolines having the structural Formula (I),

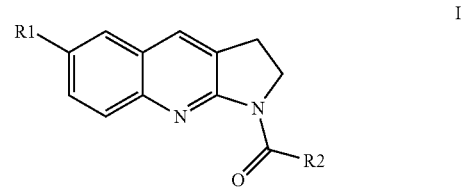

stereoisomers, tautomers, racemics, prodrugs, metabolites thereof, or pharmaceutically acceptable salt and/or solvate thereof. The meaning of R1 is independently selected from H; C1-C6 Alkyl, cyclo-Alkyl or iso-Alkyl substituents; R2 is selected from C1-C6 Alkyl, cyclo-Alkyl or iso-Alkyl; substituted or non-substituted, fused or non-fused to substituted or non-substituted aromatic ring, aryl or heteroaryl groups. The invention also relates to methods for preparing said compounds, and to pharmaceutical compositions comprising said compounds.

5 Claims, No Drawings

ANTI-CANCER AGENTS BASED ON N-ACYL-2, 3-DIHYDRO-1H-PYRROLO[2,3-B] QUINOLINE DERIVATIVES AND A METHOD OF MAKING

CONTRACTUAL ORIGIN OF THE INVENTION

The U.S. Government has certain rights in the present invention pursuant to Contract No. #3548 between the Department of Energy (DOE) (International Science and Technology Center) and the Chemical Diversity Research Institute, dated Jul. 1, 2007.

FIELD OF INVENTION

The present invention relates to novel anti-cancer agents based on derivatives of N-acyl 2,3-dihydro-1H-pyrrolo[2,3-b]quinolines that can be used in prostate cancer therapy. The present invention also relates to methods of preparing said compounds, and to pharmaceutical compositions comprising said compounds.

BACKGROUND OF THE INVENTION

Cancer is the second leading cause of human death next to coronary disease. Worldwide, millions of people die from cancer every year. In the United States alone, as reported by the American Cancer Society, cancer causes the death of well over half-million people annually, with over 1.2 million new cases diagnosed per year. While deaths from heart disease have been declining significantly, those resulting from cancer generally are on the rise. In this century, cancer is predicted to become the leading cause of death.

Prostate cancer is the number one cancer diagnosed in men today. While it occurs to certain extent throughout the world (least commonly in Eastern/Southern Asia), it is viewed as the major public health threat in Western Europe and, especially, the United States. In the US alone, it has been projected that 186,320 new cases of prostate cancer (mostly—among men over fifty) will have been diagnosed in 2008, accounting for 25% of all cancers diagnosed in men that year and 10% of the total cancer-related mortality. Appropriate diet (including dietary supplements) and exercise are currently the common themes for prostate cancer prevention while classical treatments are limited to surgery, radiation therapy, and hormone therapy.

Chemotherapy of late-stage prostate cancer is still largely experimental; however, it may lead to increased survival in the future. Specifically, small molecules as well as antibodies targeted at disrupting vital signaling pathways in cancerous cells have a potential to provide new basis for innovative treatment of prostate cancer and other proliferative disorders in the years to come. As a result, there is a strong need for new compound classes that can be used for hormone-refractory prostate cancer chemotherapy. We have discovered that derivatives of N-acyl 2,3-dihydro-1H-pyrrolo[2,3-b]quinolines are effective in vitro against androgen-independent prostate cancer cell lines.

SUMMARY OF THE INVENTION

The present invention relates to novel compounds having the structural Formula (I), stereoisomers, tautomers, racemics, prodrugs, metabolites thereof, or pharmaceutically acceptable salt and/or solvate thereof,

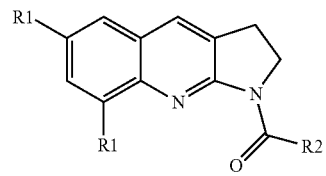

Wherein:
R1 is independently selected from H; C1-C6 Alkyl, cyclo-Alkyl or iso-Alkyl substituents;
R2 is selected from C1-C6 Alkyl, cyclo-Alkyl or iso-Alkyl; substituted or non-substituted, fused or non-fused to substituted or non-substituted aromatic ring, aryl or heteroaryl groups.

Acceptable pharmaceutical salts are hydrochloride, citrate, maleate or similar salts listed, for example in the Handbook of Pharmaceutical Salts: Properties, selection and use—Stahl P H, Wermuth C G, editors. 2002. Weinheim/Zurich: Wiley-VCH/VHCA. Typical solvate is hydrate (water).

The compounds exhibited inhibition of DU-145 cell proliferation in a dose-response manner and attracted attention due to their drug-likeness, structural simplicity, presence in their structure of two distinct types of peripheral appendages (thus allowing for informative SAR exploration), and syntheses reported in the literature for related structures.

The invention also relates to methods for preparing said compounds and to pharmaceutical compositions comprising said compounds.

DETAILED DESCRIPTION OF THE INVENTION

The present invention is a result of our ongoing efforts to find novel anti-proliferative agents as potential treatments for cancer. It was aimed at identifying new small heterocyclic molecules in the ChemDiv, Inc. collection that would be specifically inhibitory to DU-145 human prostate carcinoma cell line (a 'classical' cell line of prostate cancer), while exhibiting no non-specific (general) cytotoxicity. High-throughput screening of a highly diverse set of over 5,200 compounds over 100 analogues of 2,3-dihydro-1H-pyrrolo [2,3-b]quinolines were identified with confirmed activity. Among these, potent anti-proliferatives ring-substituted N-acyl derivatives of 2,3-dihydro-1H-pyrrolo[2,3-b]quinolines of the Formula, (I) were found.

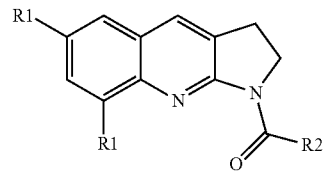

The meaning of R1, and R2 in the Formula (I) are defined as follows:
R1 is independently selected from H; C1-C6 Alkyl, cyclo-Alkyl or iso-Alkyl substituents;
R2 is selected from C1-C6 Alkyl, cyclo-Alkyl or iso-Alkyl; substituted or non-substituted, fused or non-fused to substituted or non-substituted aromatic ring, aryl or heteroaryl groups.

The compounds exhibited inhibition of DU-145 cell proliferation in dose-response manner, attracted our attention due to their drug-likeness, structural simplicity, presence in their structure of two distinct types of peripheral appendages (thus allowing for informative SAR exploration), and syntheses reported in the literature for related structures.

The preferred sequence for chemical synthesis of these compounds is shown below. The commercially available ring-substituted or non-substituted O-methyl anthranylates (A) are converted in three steps to 2,3-dihydro-1H-pyrrolo[2,3-b]quinolines (B), that by acylation (a 4$^{th}$ step) with commercially available carbonylchloride R2COCl under mild conditions produce (I) in overall low to moderate yields.

Suitable carbonylchlorides R2COCl are: 3,4,5-trimethoxy-1-benzenecarbonyl chloride; 3,4-dimethoxy-1-benzene-carbonyl chloride; 3-methoxy-1-benzene-carbonyl chloride; 2-methoxy-1-benzenecarbonyl chloride; 4-methyl-1-benzene-carbonyl chloride; 4-methyl-1-benzene-carbonyl chloride; 2-methyl-1-benzene-carbonyl chloride; 2-fluoro-1-benzene-carbonyl chloride; 2-bromo-1-benzene-carbonyl chloride; 3-fluoro-1-benzene-carbonyl chloride; and 4-bromo-1-benzene-carbonyl chloride.

Suitable O-methyl anthranylates (A) are: O-methyl anthranylate (Aldrich, Cat. Nr. M29703); O-methyl 5-methyl-anthranylate (ENAMINE-BB, Cat. Nr. EN300-42954); and O-methyl 3-methyl-anthranylate (ENAMINE-BB, Cat. Nr. EN300-43096).

intermediate product that was purified by column chromatography on silica gel using DCM-EtOAc (dichloromethane and ethyl acetate) with a different gradient as a mobile phase. Typical yields of R1-substituted N-benzyl-4-chloro-2,3-dihydro-1H-pyrrolo[2,3-b]quinolines (last formula, top line) vary in a range of 55-85%. The latter were subjected to hydrogenolysis—at 5 atm. H$_2$ in methanol solution at room temperature using 5% of Pd/C (10 wt. % palladium on carbon) as a catalyst to give 2,3-dihydro-1H-pyrrolo[2,3-b]quinolines (B). The completion of hydrogenolysis was monitored by thin-layer chromatography on silica gel using 10% ethyl acetate in dichloromethane as a mobile phase.

The latter have been further acylated at room temperature. In a typical load 2 mmol of B was dissolved in dry pyridine (20 mL) at room temperature, 4-(dimethylamino)pyridine (DMAP) (2 mmol) was added as a base followed by addition of R2COCl (a carbonyl chloride) (2 mmol) under vigorous stifling. The reaction mixture was quenched by addition of 10% aq. HCl (50 mL), vigorously stirred for 10 min, extracted with ethyl acetate (3 times per 20 mL) and upon solvent removal, purified by column chromatography on silica gel using DCM-EtOAc (dichloromethane and ethyl acetate) with a different gradient as a mobile phase to give the target N-acyl-2,3-dihydro-1H-pyrrolo[2,3-b]quinolines (I) in overall yields varied in the range of 19-77% as off-white to yellow colored solids of >95% purity, confirmed by $^1$H-NMR analy-

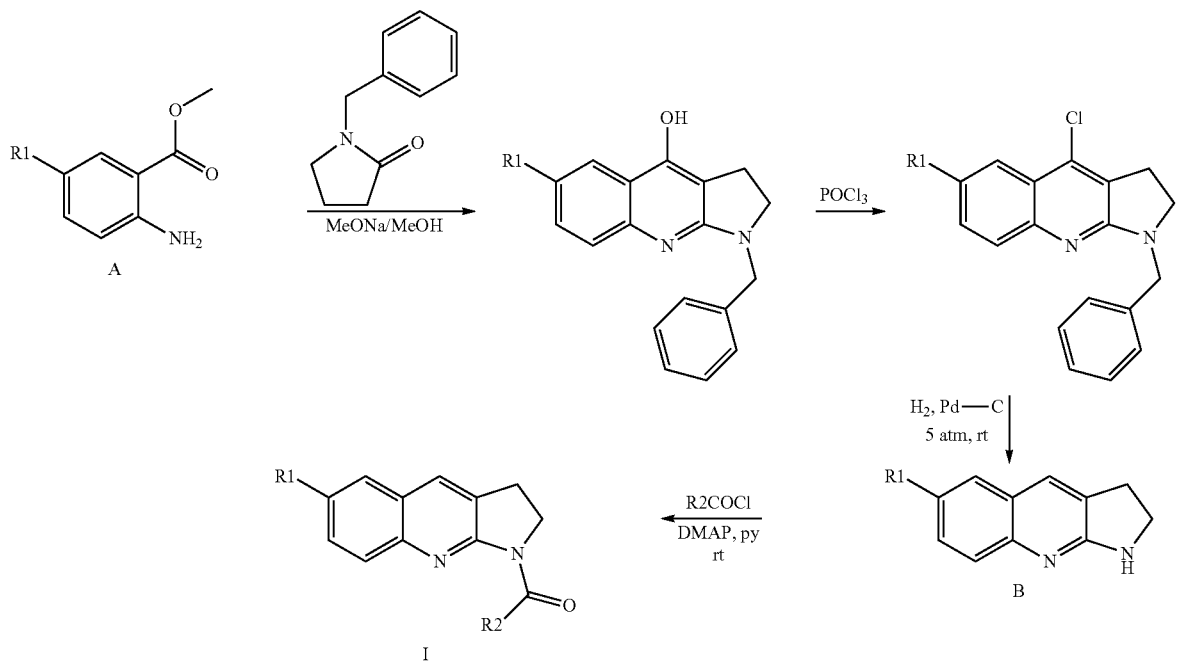

The General Synthetic Protocol:

to a stirred solution of O-methyl anthranylates (A) (0.02 mol) and N-benzylpyrrolidone (0.025 mol) in dry methanol (100 mL), a solution of sodium methylate (MeONa) (0.03 mol) in dry methanol (MeOH) (30 mL) was added drop-wise over a period of 1 hr. at ambient temperature, whereupon the reaction mixture was allowed to stir overnight followed by evaporation of the methanol under reduced pressure (20-100 mbar). The obtained residue was dissolved of in phosphoryl chloride (POCl$_3$) (100 mL) and heated to reflux for 1-3 hr. Evaporation of an excess of phosphoryl chloride gave an sis of the solutions of 5 mg of I in DMSO (dimethyl sulfoxide) (0.25 mL) using Bruker DPX-400 instrument (400 MHz H1 NMR Frequency).

Suitable quinolines (B) subject to hydrogenolysis are: 2,3-dihydro-1H-pyrrolo[2,3-b]quinoline; 6-methyl-2,3-dihydro-1H-pyrrolo[2,3-b]quinoline; 6-methyl-2,3-dihydro-1H-pyrrolo[2,3-b]quinoline; or 8-methyl-2,3-dihydro-1H-pyrrolo[2,3-b]quinoline.

Suitable R2COCl carbonyl chlorides are: 3,4,5-trimethoxy-1-benzenecarbonyl chloride; 3,4-dimethoxy-1-benzene-carbonyl chloride; 3-methoxy-1-benzene-carbonyl chloride; 2-methoxy-1-benzenecarbonyl chloride; 4-methyl-1-benzenecarbonyl chloride; 4-methyl-1-benzene-carbonyl chloride; 2-methyl-1-benzene-carbonyl chloride; 2-fluoro-1-benzene-carbonyl chloride; 2-bromo-1-benzene-carbonyl chloride; 3-fluoro-1-benzene-carbonyl chloride; and 4-bromo-1-benzene-carbonyl chloride.

Suitable N-acyl-2,3-dihydro-1H-pyrrolo[2,3-b]quinolines (I) are: 2,3-dihydro-1H-pyrrolo[2,3-b]quinolin-1-yl(3,4,5-trimethoxyphenyl)methanone; (3,4-dimethoxyphenyl)(6-methyl-2,3-dihydro-1H-pyrrolo[2,3-b]quinolin-1-yl)methanone; (3-methoxyphenyl)(6-methyl-2,3-dihydro-1H-pyrrolo[2,3-b]quinolin-1-yl)methanone; 2,3-dihydro-1H-pyrrolo[2,3-b]quinolin-1-yl(2-methoxyphenyl)methanone; (6-methyl-2,3-dihydro-1H-pyrrolo[2,3-b]quinolin-1-yl)(4-methylphenyl)methanone; (2-methoxyphenyl)(8-methyl-2,3-dihydro-1H-pyrrolo[2,3-b]quinolin-1-yl)methanone; (8-methyl-2,3-dihydro-1H-pyrrolo[2,3-b]quinolin-1-yl)(2-methylphenyl)methanone; (2-fluorophenyl)(8-methyl-2,3-dihydro-1H-pyrrolo[2,3-b]quinolin-1-yl)methanone; (2-bromophenyl)(2,3-dihydro-1H-pyrrolo[2,3-b]quinolin-1-yl)methanone; (3-fluorophenyl)(8-methyl-2,3-dihydro-1H-pyrrolo[2,3-b]quinolin-1-yl)methanone; (2-bromophenyl)(8-methyl-2,3-dihydro-1H-pyrrolo[2,3-b]quinolin-1-yl)methanone; and (4-bromophenyl)(6-methyl-2,3-dihydro-1H-pyrrolo[2,3-b]quinolin-1-yl)methanone.

Example 1

2,3-dihydro-1H-pyrrolo[2,3-b]quinolin-1-yl(3,4,5-trimethoxyphenyl)methanone was obtained from reacting 2,3-dihydro-1H-pyrrolo[2,3-b]quinoline and 3,4,5-trimethoxy-1-benzenecarbonyl chloride, in 44% overall yield. $^1$H-NMR (DMSO-d$^6$) δ: 8.10-6.80 (7H, C$_{Aryl}$H), 4.43, 3.32 (4H, t, t, CH$_2$—CH$_2$), 3.81, 3.71 (3H, 6H, s, s, —OCH$_3$).

Example 2

(3,4-dimethoxyphenyl)(6-methyl-2,3-dihydro-1H-pyrrolo[2,3-b]quinolin-1-yl)methanone was obtained from reacting 6-methyl-2,3-dihydro-1H-pyrrolo[2,3-b]quinoline and 3,4-dimethoxy-1-benzene-carbonyl chloride, in 77% overall yield. $^1$H-NMR (DMSO-d$^6$) δ: 7.87-6.90 (7H, C$_{Aryl}$H), 4.18, 3.24 (4H, t, t, CH$_2$—CH$_2$), 3.67, 3.58 (3H, 3H, s, s, —OCH$_3$), 2.43 (3H, s, CH$_3$).

Example 3

(3-methoxyphenyl)(6-methyl-2,3-dihydro-1H-pyrrolo[2,3-b]quinolin-1-yl)methanone was obtained from reacting 6-methyl-2,3-dihydro-1H-pyrrolo[2,3-b]quinoline and 3-methoxy-1-benzene-carbonyl chloride, in 19% overall yield. $^1$H-NMR (DMSO-d$^6$) δ: 7.86-7.04 (8H, C$_{Aryl}$H), 4.20, 3.25 (4H, t, t, CH$_2$—CH$_2$), 3.76 (3H, s, —OCH$_3$), 2.42 (3H, s, CH$_3$).

Example 4

2,3-dihydro-1H-pyrrolo[2,3-b]quinolin-1-yl(2-methoxyphenyl)methanone was obtained from reacting 2,3-dihydro-1H-pyrrolo[2,3-b]quinoline and 2-methoxy-1-benzenecarbonyl chloride, in 19% overall yield. $^1$H-NMR (DMSO-d$^6$) δ: 8.15-6.95 (9H, C$_{Aryl}$H), 4.21, 3.25 (4H, t, t, CH$_2$—CH$_2$), 3.51 (3H, s, —OCH$_3$).

Example 5

(6-methyl-2,3-dihydro-1H-pyrrolo[2,3-h] quinolin-1-yl)(4-methylphenyl)methanone was obtained from reacting 6-methyl-2,3-dihydro-1H-pyrrolo[2,3-b]quinoline and 4-methyl-1-benzene-carbonyl chloride, in 71% overall yield. $^1$H-NMR (DMSO-d$^6$) δ: 7.87-7.12 (8H, C$_{Aryl}$H), 4.17, 3.24 (4H, t, t, CH$_2$—CH$_2$), 3.76 (3H, s, —OCH$_3$), 2.42, 2.44 (3H, 3H, s, s, CH$_3$, CH$_3$).

Example 6

(2-methoxyphenyl)(8-methyl-2,3-dihydro-1H-pyrrolo[2,3-b]quinolin-1-yl)methanone was obtained from reacting 8-methyl-2,3-dihydro-1H-pyrrolo[2,3-b]quinoline and 2-methoxy-1-benzene-carbonyl chloride, in 51% overall yield. $^1$H-NMR (DMSO-d$^6$) δ: 7.88-6.96 (8H, C$_{Aryl}$H), 4.24, 3.28 (4H, t, t, CH$_2$—CH$_2$), 3.54 (3H, s, —OCH$_3$), 1.82 (3H, s, CH$_3$).

Example 7

(8-methyl-2,3-dihydro-1H-pyrrolo[2,3-h] quinolin-1-yl)(2-methylphenyl)methanone was obtained from reacting 8-methyl-2,3-dihydro-1H-pyrrolo[2,3-b]quinoline and 2-methyl-1-benzene-carbonyl chloride, in 68% overall yield. $^1$H-NMR (DMSO-d$^6$) δ: 7.92-7.14 (8H, C$_{Aryl}$H), 4.27, 3.31 (4H, t, t, CH$_2$—CH$_2$), 3.54 (3H, s, —OCH$_3$), 2.23, 1.78 (3H, 3H, s, s, CH$_3$, CH$_3$).

Example 8

(2-fluorophenyl)(8-methyl-2,3-dihydro-1H-pyrrolo[2,3-b]quinolin-1-yl)methanone was obtained from reacting 8-methyl-2,3-dihydro-1H-pyrrolo[2,3-b]quinoline and 2-fluoro-1-benzene-carbonyl chloride, in 64% overall yield. $^1$H-NMR (DMSO-d$^6$) δ: 7.95-7.14 (8H, C$_{Aryl}$H), 4.26, 3.30 (4H, t, t, CH$_2$—CH$_2$), 1.83 (3H, s, CH$_3$).

Example 9

(2-bromophenyl)(2,3-dihydro-1H-pyrrolo[2,3-b]quinolin-1-yl)methanone was obtained from reacting 2,3-dihydro-1H-pyrrolo[2,3-b]quinoline and 2-bromo-1-benzene-carbonyl chloride, in 62% overall yield. $^1$H-NMR (DMSO-d$^6$) δ: 8.00-7.00 (8H, C$_{Aryl}$H), 4.26, 3.31 (4H, t, t, CH$_2$—CH$_2$).

Example 10

(3-fluorophenyl)(8-methyl-2,3-dihydro-1H-pyrrolo[2,3-h] quinolin-1-yl)methanone was obtained from reacting 8-methyl-2,3-dihydro-1H-pyrrolo[2,3-b]quinoline and 3-fluoro-1-benzene-carbonyl chloride, in 55% overall yield. $^1$H-NMR (DMSO-d$^6$) δ: 7.92-7.17 (8H, C$_{Aryl}$H), 4.21, 3.27 (4H, t, t, CH$_2$—CH$_2$), 1.90 (3H, s, CH$_3$).

Example 11

(2-bromophenyl)(8-methyl-2,3-dihydro-1H-pyrrolo[2,3-b]quinolin-1-yl)methanone was obtained from reacting 8-methyl-2,3-dihydro-1H-pyrrolo[2,3-b]quinoline and 2-bromo-1-benzene-carbonyl chloride, in 48% overall yield. $^1$H-NMR (DMSO-d$^6$) δ: 7.94-7.16 (8H, C$_{Aryl}$H), 4.28, 3.32 (4H, t, t, CH$_2$—CH$_2$), 1.80 (3H, s, CH$_3$).

Example 12

(4-bromophenyl)(6-methyl-2,3-dihydro-1H-pyrrolo[2,3-b]quinolin-1-yl)methanone was obtained from reacting 6-methyl-2,3-dihydro-1H-pyrrolo[2,3-b]quinoline and 4-bromo-1-benzene-carbonyl chloride, in 75% overall yield.

$^1$H-NMR (DMSO-d$^6$) δ: 7.98-7.14 (8H, C$_{Aryl}$H), 4.26, 3.26 (4H, t, t, CH$_2$—CH$_2$), 2.41 (3H, s, CH$_3$).

Among the 12 compounds in the above examples, 7 compounds showed IC$_{50}$ values for proliferation inhibition of DU-145 cells <20 uM, and among them 3 examples were <1 uM. IC$_{50}$ represents the concentration of a drug that is required for 50% inhibition in vitro. As shown in Table 1, the compositions at the beginning of the table are more effective inhibitors than those at the end of the table.

TABLE 1

| Example # | IC$_{50}$, μM |
|---|---|
| 1 | 0.114 |
| 2 | 0.183 |
| 3 | 0.613 |
| 4 | 3.620 |
| 5 | 10.31 |
| 6 | 16.15 |
| 7 | 17.19 |
| 8 | 133.5 |
| 9 | 238.1 |
| 10 | 4 400 |
| 11 | 15 000 |
| 12 | — |

Protocol for Cell Proliferation Assay:

This homogeneous assay involves simply adding a single reagent, the Alamar-Blue, to the cell culture and measuring the fluorescence intensity (excitation wavelength=530 nm, emission wavelength=590 nm) after an incubation step. The Alamar-Blue reagent utilizes the redox dye resazurin, which is not fluorescent, but upon reduction by metabolically active cells is converted into a highly fluorescent product (resorufin). A decrease in fluorescence in the presence of a test compound indicates reduced proliferation. This change in signal is proportional to the number of viable cells and used as a measure of relative cytotoxicity. Therefore, the fluorescence intensity observed in this assay is a true measure of the viable proliferative cells.

Reagents
  2 mM stock of Paclitaxel in DMSO.
  DMSO (Panreac, Cat. number 141954.1611)
  Resazurin sodium salt (Sigma, R-7071). 50 mM stock in DMSO.
Equipment
  Biomek FX Laboratory Automated Workstation (Beckman Coulter Inc., Fullerton, Calif.)
  CO$_2$ incubator (VWR Science, USA)
  Bright line Hemacytometer (Z359629, Sigma, IL, USA)
Materials
  384-deep well plates (Greiner, N° 781270)
  384-well optical bottom tissue culture plates (Greiner, No. 82051-282)
Propagation
CONDITIONS: 37° C., air 95%; carbon dioxide (CO$_2$) 5%, humidified atmosphere.
Subculturing:
  Cells were grown in 175 cm$^2$ flasks to 90-100% of confluency.
  Culture medium (RPMI-1640 (Paneco, C310)+10% fetal bovine serum (FBS)) was aspirated and cell layer was briefly rinsed with 0.53 mM EDTA (ethylenediaminetetraacetic acid) solution to remove all traces of serum.
  2 ml of 0.2% trypsin/0.53 mM EDTA solution was added to cells.
  Flasks were returned to incubator for 5 min to allow cells detachment.
  Add 6.0 ml of culture medium.
  Single cell suspension was created by gently pipetting.
  Cells are counted using a Hematocytometer and suspension with desirable cell concentration is prepared.

To test proliferation inhibition DU-145 cells were plated in 384-well plate at the density 4000 cells/well. Next day 4 mM solutions of compounds in DMSO were diluted 100 times in medium and added to cells to final concentration 20 uM (40 ul of cells+40 ul of compounds). Taxol at final concentration 1 uM was used as positive control. Cells were incubated with compounds for 3 days. After that Alamar-Blue was added to cells to final concentration of 50 uM. After incubation for 4-6 hours at 37° C., fluorescence in plate was read using fluorescence plate reader Wallac 1420 (530 nm excitation filter, 590 nm emission filter). Proliferation inhibition was calculated using formula:

% INH=100*(($F_{negative}$−compound signal)/($F_{negative}$−$F_{positive}$)), $F_{negative}$—DMSO was added to cells (viable cells)
$F_{positive}$—taxol (1 uM) was added to cells (number of cells at the first day of incubation)

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

The invention claimed is:

1. A method of preparing N-acyl derivatives of 2,3-dihydro-1H-pyrrolo[2,3-b]quinolines having the structural Formula (I),

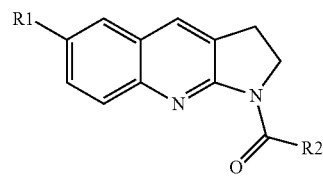

stereoisomers, tautomers, racemics, or pharmaceutically acceptable salt thereof, wherein
  R1 is independently selected from H or a straight chain or branched C1-C6 Alkyl,
  R2 is selected from C1-C6 Alkyl, substituted or nonsubstituted, fused or non-fused to substituted or non-substituted aromatic ring, aryl or heteroaryl groups, comprising the step of:
  reacting a 2,3-dihydro-1H-pyrrolo[2,3-b]quinoline with a carbonyl chloride in the presence of 4-(dimethylamino)pyridine and pyridine at about room temperature,
  wherein the 2,3-dihydro-1H-pyrrolo[2,3-b]quinoline has the formula:

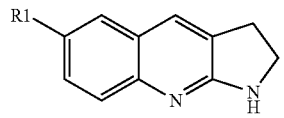

wherein R1 is defined as above; and,
wherein the carbonyl chloride has the formula R2COCl and R2 is defined as above.

2. The method of claim 1, wherein said suitable 2,3-dihydro-1H-pyrrolo[2,3-b]quinolines are selected from:
- 2,3-dihydro-1H-pyrrolo[2,3-b]quinoline;
- 6-methyl-2,3-dihydro-1H-pyrrolo[2,3-b]quinoline; or
- 6-methyl-2,3-dihydro-1H-pyrrolo[2,3-b]quinoline.

3. The method of claim 2, wherein said suitable carbonyl chlorides have the formula R2COCl.

4. The method of claim 3 wherein the carbonyl chloride is selected from the group consisting of:
- 3,4,5-trimethoxy-1-benzenecarbonyl chloride;
- 3,4-dimethoxy-1-benzene-carbonyl chloride;
- 3-methoxy-1-benzene-carbonyl chloride;
- 2-methoxy-1-benzenecarbonyl chloride;
- 4-methyl-1-benzene-carbonyl chloride;
- 4-methyl-1-benzene-carbonyl chloride;
- 2-methyl-1-benzene-carbonyl chloride;
- 2-fluoro-1-benzene-carbonyl chloride;
- 2-bromo-1-benzene-carbonyl chloride;
- 3-fluoro-1-benzene-carbonyl chloride; or
- 4-bromo-1-benzene-carbonyl chloride.

5. The method of claim 1 wherein the carbonyl chloride is selected from the group consisting of:
- 3,4,5-trimethoxy-1-benzenecarbonyl chloride;
- 3,4-dimethoxy-1-benzene-carbonyl chloride;
- 3-methoxy-1-benzene-carbonyl chloride;
- 2-methoxy-1-benzenecarbonyl chloride;
- 4-methyl-1-benzene-carbonyl chloride;
- 4-methyl-1-benzene-carbonyl chloride;
- 2-methyl-1-benzene-carbonyl chloride;
- 2-fluoro-1-benzene-carbonyl chloride;
- 2-bromo-1-benzene-carbonyl chloride;
- 3-fluoro-1-benzene-carbonyl chloride; or
- 4-bromo-1-benzene-carbonyl chloride.

* * * * *